United States Patent
Fisker et al.

(12)

(10) Patent No.: US 10,242,128 B2
(45) Date of Patent: Mar. 26, 2019

(54) TOOLS FOR CUSTOMIZED DESIGN OF DENTAL RESTORATIONS

(71) Applicant: 3SHAPE A/S, Copenhagen K (DK)

(72) Inventors: Rune Fisker, Virum (DK); Tais Clausen, Klagshamn (SE); Nikolaj Deichmann, Klagshamn (SE)

(73) Assignee: 3SHAPE A/S, Copenhagen K (DK)

( * ) Notice: Subject to any disclaimer, the term of this patent is extended or adjusted under 35 U.S.C. 154(b) by 0 days.

(21) Appl. No.: 14/972,999

(22) Filed: Dec. 17, 2015

(65) Prior Publication Data

US 2016/0103935 A1 Apr. 14, 2016

Related U.S. Application Data

(63) Continuation of application No. 14/730,601, filed on Jun. 4, 2015, now Pat. No. 9,289,276, which is a
(Continued)

(30) Foreign Application Priority Data

Sep. 18, 2008 (DK) .................................. 2008 01310

(51) Int. Cl.
*A61C 5/77* (2017.01)
*G06F 17/50* (2006.01)
(Continued)

(52) U.S. Cl.
CPC ................ *G06F 17/50* (2013.01); *A61C 5/77* (2017.02); *A61C 13/0004* (2013.01);
(Continued)

(58) Field of Classification Search
None
See application file for complete search history.

(56) References Cited

U.S. PATENT DOCUMENTS 5,674,069 A 10/1997 Osorio
5,815,154 A 9/1998 Hirschtick et al.
(Continued)

FOREIGN PATENT DOCUMENTS

WO WO 2008/066891 A2 6/2008

OTHER PUBLICATIONS

3Shape Dental Designer 2005-2 User Manual, 2005, pp. 1-39.
(Continued)

*Primary Examiner* — Said Broome
(74) *Attorney, Agent, or Firm* — Buchanan Ingersoll & Rooney P.C.

(57) ABSTRACT

Tools in a system for the design of customized three-dimensional models of dental restorations for subsequent manufacturing. Dental restorations such as implant abutments, copings, crowns, wax-ups, bridge frameworks. Moreover, a computer-readable medium for implementing such a system on a computer. A system for designing at least one dental restoration, said system including: a display, means for acquiring and displaying a three dimensional dental restoration model of the dental restoration, and means for displaying a plurality of control points, each of the control points corresponding to a respective location on the dental restoration model, and each of said control points enabling manual customization of the dental restoration model.

29 Claims, 6 Drawing Sheets

Related U.S. Application Data continuation of application No. 14/222,761, filed on Mar. 24, 2014, now Pat. No. 9,075,937, which is a continuation of application No. 13/119,514, filed as application No. PCT/DK2009/050243 on Sep. 17, 2009, now Pat. No. 8,718,982.

(60) Provisional application No. 61/098,255, filed on Sep. 19, 2008.

(51) Int. Cl.
  *B33Y 50/00* (2015.01)
  *B33Y 80/00* (2015.01)
  *A61C 13/00* (2006.01)
  *A61C 8/00* (2006.01)

(52) U.S. Cl.
  CPC .............. *B33Y 50/00* (2014.12); *B33Y 80/00* (2014.12); *A61C 8/005* (2013.01)

(56) References Cited

U.S. PATENT DOCUMENTS

| | | | | |
|---|---|---|---|---|
| 2002/0177108 | A1* | 11/2002 | Pavlovskaia | A46B 15/0002 433/215 |
| 2003/0007016 | A1* | 1/2003 | Laffey | G06F 3/04812 715/861 |
| 2004/0067465 | A1* | 4/2004 | Schomann | A61C 13/0004 433/26 |
| 2005/0089822 | A1* | 4/2005 | Geng | A61C 13/0004 433/215 |
| 2005/0271996 | A1 | 12/2005 | Sporbert et al. | |
| 2008/0261165 | A1* | 10/2008 | Steingart | A61C 13/0004 433/24 |
| 2009/0042167 | A1 | 2/2009 | Van Der Zel | |

OTHER PUBLICATIONS

3Shape Dental Designer 2007-1 User Manual, 2007, pp. 1-113.
Martin Vogel., "AutoCad LT Tutorial—Seite 27," http://www.martinvogel.de/acadlt/autocad-anleitung-tutorial-einfuehrung-27.htm, 2008, p. 27, and English language translation of webpage.
Martin Vogel., "AutoCad LT Tutorial—Seite 10," http://www.martinvogel.de/acadlt/autocad-anleitung-tutorial-einfuehrung-10.htm, 2008, p. 10, and English language translation of webpage.
Martin Vogel., "AutoCad LT Tutorial—Seite 18," http://www.martinvogel.de/acadlt/autocad-anleitung-tutorial-einfuehrung-18.htm, 2008, p. 18, and English language translation of webpage.
Martin Vogel., "AutoCad LT Tutorial—Seite 19," http://www.martinvogel.de/acadlt/autocad-anleitung-tutorial-einfuehrung-19.htm, 2008, p. 19, and English language translation of webpage.
Martin Vogel., "AutoCad LT Tutorial—Seite 6," http://www.martinvogel.de/acadlt/autocad-anleitung-tutorial-einfuehrung-6.htm, 2008, p. 6, and English language translation of webpage.
AutoCAD ("AutoCAD LT 2006: The Definitive Guide"). Wordware Publishing. INC., 2005., 11 Pages.
Official Action issued in corresponding Chinese Patent Application No. 200980136606.5, dated Jan. 31, 2013, and English translation thereof.
International Search Report for PCT/DK2009/050243, dated Mar. 5, 2010.

* cited by examiner

TOOLS FOR CUSTOMIZED DESIGN OF DENTAL RESTORATIONS

CROSS-REFERENCE TO RELATED APPLICATIONS

The present application is a continuation of U.S. application Ser. No. 14/730,601, filed on Jun. 4, 2015, which is a continuation of U.S. application Ser. No. 14/222,761, filed on Mar. 24, 2014, now U.S. Pat. No. 9,075,937, which is a continuation of U.S. application Ser. No. 13/119,514, filed on May 31, 2011, now U.S. Pat. No. 8,718,982, which is a U.S. national stage application of International Application No. PCT/DK2009/050243, filed on Sep. 17, 2009, and which claims the benefit of U.S. Provisional Application No. 61/098,255, filed on Sep. 19, 2008, and which also claims the priority of Danish Patent Application No. PA 2008-01310, filed on Sep. 18, 2008. The contents of U.S. application Ser. No. 14/730,601, U.S. application Ser. No. 14/222,761, U.S. application Ser. No. 13/119,514, International Application No. PCT/DK2009/050243, U.S. Provisional Application No. 61/098,255, and Danish Patent Application No. PA 2008-01310 are incorporated herein by reference in their entirety.

FIELD OF THE DISCLOSURE

The present disclosure relates to tools in a system for the design of customized three-dimensional models of dental restorations for subsequent manufacturing. Dental restorations such as implant abutments, copings, crowns, wax-ups, bridge frameworks. Moreover, the disclosure relates to a computer-readable medium for implementing such a system on a computer.

BACKGROUND OF THE DISCLOSURE

The present disclosure is related to the field of designing and manufacturing of dental restorations such as crowns, bridges, copings, abutments and implants. When a patient requires a dental restoration the dentist will prepare the teeth e.g. a damaged tooth is grinded down to make a preparation where the crown is glued onto. An alternative treatment is to insert implants (titanium screws) into the jaw of the patient and mount crowns or bridges on the implants.

CAD technology for manufacturing dental restorations is rapidly expanding resulting in improved quality, reduced cost and facilitation of the possibility to manufacture in attractive materials otherwise not available. The first step in the CAD manufacturing process is to create a 3-dimensional dental model of the patient's teeth. This is provided by 3D scanning of one or both of the dental gypsum models or by scanning impressions of the teeth. The 3-dimensional replicas of the teeth are imported into a CAD program, where the entire dental restoration or a bridge substructure is designed. The final restoration 3D design is then manufactured e.g. using a milling machine, 3D printer, rapid prototyping manufacturing or other manufacturing equipment. Accuracy requirements for the dental restorations are very high otherwise the dental restoration will not be visual appealing, fit onto the teeth, could cause pain or cause infections.

Systems for designing dental restorations are known in the art, e.g. 3Shape DentalDesigner™ and 3Shape AbutmentDesigner™, which are generally used by dental specialists such as dental technicians. Users of such design tool systems are working with a three dimensional dental model of the patient trying to fit the dental restoration model into the dental model. During dental restoration of a patients teeth the typical procedure could be to secure an implant abutment in the jaw of the patient, a coping is then attached (e.g. by glue) to the abutment and finally a crown is glued onto the coping. However, both abutment, coping and crown must be designed to fit the patient, both physically and visually. I.e. the abutment, the coping and the crown must be customized for each tooth of each patient.

In the following the term "dental restoration" can be an implant abutment, a coping, a crown or any combination of these. Correspondingly a "dental restoration model" can be an abutment model, a coping model, a crown model or any combination of these.

In the design phase of a dental restoration a three dimensional model of the dental restoration is typically provided by the system and the task of the dental specialist is to shape the dental restoration model to provide a perfect fit in the dental model, whereby the patient can end up with a tooth implant that matches the other teeth of the patient. A dental specialist (i.e. a user of the system) is typically working with a dental model with at least one attached dental restoration model on a screen and the 3D models can typically be rotated around any axis, zoomed, panned and the like. Thus the user will typically be able to specify and change the orientation and viewing angle of the dental model and the dental restoration model. The task of a user is to shape and customize the dental restoration model into the dental model by translating, rotating, dragging, tilting, widening and/or narrowing the 3D dental restoration model (which preferably is fixed in the dental model). This is typically provided by use of an electronic screen pointing tool, such as a mouse, a ball pen or the like. In the following any reference to a "mouse cursor" or a "mouse marker" is a reference to the element on the screen representing the electronic screen pointing tool.

The dental restoration model can be customizably shaped by means of the pointing tool by shaping ("dragging") the dental restoration model with origin in specific points on the dental restoration model. These points are in the following termed "control points" and can be seen in FIG. 1. The control points are typically located in carefully and preferably automatically selected positions on the dental restoration model. For example in FIG. 1 showing an abutment model where the control points are located on the top center, each of the four sides and around the lower bottom rim (i.e. the lower collar of the abutment).

SUMMARY

When creating a dental restoration model certain rules must be applied, for example in terms of distance to adjacent teeth and gingival ridge and integration into the gingival. Measuring and checking these distances can be a cumbersome process during the design and creation of a dental restoration model, thus an object of the disclosure is to provide an intuitive and quick indication of distances between neighboring and adjacent objects in the process of creating a custom dental restoration.

This is achieved by a system for designing at least one dental restoration, said system having a display, such as a computer screen, and comprising:

means for acquiring and displaying a three dimensional model of the dental restoration and/or a three dimensional dental model wherein the dental restoration must be fitted, means for displaying a plurality of control points at the three dimensional model of the dental restoration, the control points preferably located at the edges of the dental restoration model and each of said control points providing means for manually customizing the dental restoration model.

The disclosure further relates to method for designing at least one dental restoration at a display, a display such as a computer screen, said method comprising the steps of:

acquiring and displaying a three dimensional model of the dental restoration and/or a three dimensional dental model wherein the dental restoration must be fitted, displaying a plurality of control points at the three dimensional model of the dental restoration, the control points preferably located at the edges of the dental restoration model and each of said control points providing means for manually customizing the dental restoration model.

In a further embodiment of the disclosure means for displaying an arrow at at least one of the control points is provided. The length of said arrow is preferably determined by a user defined value, whereby the distance between the dental restoration model and neighboring objects can be measured or indicated.

Thus, for a dental specialist in the process of creating a dental restoration this disclosure provides a quick real-time distance indicator when shaping the dental restoration model. For example when the dental specialist is varying the width of the dental restoration model by dragging the model in a control point, an arrow with origin in the specific control point will, by the length of said arrow, indicate a certain distance from the dental restoration model. The length of the arrow is determined by the user (i.e. the dental specialist in this case), thus if the user in advance knows that the distance from the dental restoration to the neighboring tooth should be 1.5 mm, the length of the arrow is specified to 1.5 mm and when widening the dental restoration model by dragging a control point, the arrow with origin in said control point will indicate for the user when the distance to the neighboring tooth is 1.5 mm. Thus, adjusting a dental restoration model to the correct width can be provided within seconds by the system and method according to the disclosure.

In a further embodiment of the disclosure means for displaying a grid at at least one control point is comprised. The size of the grid is determined by a user defined value. This grid provides the user with yet another way of measuring the distance to adjacent objects. The grid can have the appearance of a square divided into smaller and preferably equally sized squares, for example the grid can be a square of height and width of 1 mm divided into 4 squares of height and width 0.5 mm, or 16 squares of height and width 0.25 mm. An example of a grid can be seen in FIG. 7. Unlike an arrow a grid can provide an indication of a distance between two unaligned points, i.e. the grid can provide the orthographic projection distance between two points.

A second embodiment of the disclosure relates to a system for designing at least one dental restoration, said system having a display, such as a computer screen, and comprising:

means for acquiring and displaying a three dimensional model of the dental restoration and/or a three dimensional dental model wherein the dental restoration must be fitted, and means for displaying an arrow adjacent to the edge of the dental restoration model, the length of said arrow determined by a user defined value, whereby the distance between the dental restoration model and neighboring objects can be measured or indicated, and/or means for displaying a grid adjacent to the edge of the dental restoration model, the size of said grid determined by a user defined value, whereby the distance between the dental restoration model and neighboring objects can be measured or indicated.

Correspondingly the disclosure relates to a method for designing at least one dental restoration at a display, a display such as a computer screen, said method comprising the steps of:

acquiring and displaying a three dimensional model of the dental restoration and/or a three dimensional dental model wherein the dental restoration must be fitted, and displaying an arrow adjacent to the dental restoration model, the length of said arrow determined by a user defined value, whereby the distance between the dental restoration model and neighboring objects can be measured or indicated, and/or displaying a grid adjacent to the dental restoration model, the size of said grid determined by a user defined value, whereby the distance to neighboring objects can be indicated.

Preferably the arrow and/or the grid is located at the edge of the dental restoration model, preferably pointing towards a neighboring object. Naturally the arrow and/or the grid may also be displayed adjacent to, preferably at the edge of, a neighboring object (such as the dental model).

DETAILED DESCRIPTION OF THE DISCLOSURE

If each control point of the dental restoration model is showing an arrow or a grid, a confusing picture will be provided to the user. Thus in a preferred embodiment of the invention an arrow or a grid of a control point is only displayed under certain circumstances, preferably when the control point is activated. In a preferred embodiment activation of a control point is provided when the mouse cursor is close to a control point. "Close to" in the meaning of within a certain number of pixels on the screen and/or within a certain distance from the control point. Thus, an arrow or a grid of a control point is preferably only visible when the mouse marker is close to said control point. In another embodiment of the invention an arrow or a grid is only visible when the mouse marker is close to the origin of said arrow or grid.

In specific embodiments of the invention an arrow or grid is only visible when the mouse cursor is within a distance of preferably 10 pixels from a corresponding control point and/or the origin of said arrow or grid, such as within a distance of 100 pixels, such as within a distance of 80 pixels, such as within a distance of 60 pixels, such as within a distance of 40 pixels, such as within a distance of 30 pixels, such as within a distance of 20 pixels, such as within a distance of 15 pixels, such as within a distance of 12 pixels, such as within a distance of 8 pixels, such as within a distance of 6 pixels, such as within a distance of 5 pixels, such as within a distance of 4 pixels, such as within a distance of 3 pixels, such as within a distance of 2 pixels, such as within a distance of 1 pixel from a corresponding control point and/or the origin of said arrow or grid.

The length of an arrow or the size of a grid can be defined by the user, e.g. by a graphical menu. However, means for varying the length of an arrow or the size of a grid can advantageously be provided to the user simultaneous with an activation of a control point. Thus, in a preferred embodiment of the system the length of an arrow or the size of a grid can be adjusted when a control point is activated. This adjustment can preferably be provided by means of user interaction, such as a screen pointing tool action, e.g. by turning the scroll wheel of the mouse. In this case a specific revolution of the scroll wheel is transferred to a specific increase or decrease of the length of the arrow or the size of the grid. For example a revolution of 5 degrees of the scroll wheel could correspond to a change in 0.1 mm in the length of an arrow or the size of a grid. Correspondingly for other types of screen pointing tools with or without variable buttons, scroll wheels and/or the equivalents of that. For practical reasons the numerical value of the length of the arrow or the size of the grid may be displayed to the user on the screen concurrently with the user interaction, e.g. the user can see the numerical value of the length of an arrow while turning the scroll wheel of the mouse.

When customizing the dental restoration model in a dental model it might be necessary to both expand, tilt and rotate the dental restoration model. A solution where each control point has only one functionality (e.g. the functionality of "rotation") requires a great number of control points on the dental restoration model, possibly creating a confusing Graphical User Interface (GUI) for the user. In a preferred embodiment of the invention the functionality of at least one control point is variable, i.e. at least one of the control points has more than one function and the user can shift between these functions. Shifting the functionality of a control point can be provided in numerous ways in the GUI (e.g. by means of menus, buttons and/or the like). However, for the user a quick shift in functionality is advantageous, preferably without moving the mouse away from the control point, i.e. the user can preferably change the functionality of a control point when said control point is activated. For practical reasons the specific functionality of a control point can be indicated by a symbol on the screen to ease the user interaction. E.g. a specific symbol near a control point corresponds to a specific current functionality of the control point. Examples of functionality symbols are illustrated in FIG. 14.

Furthermore, the functionality of a control point can preferably be changed by some specific activation of the mouse. A known specific activation is the "double-click" of a mouse button. Another specific activation is a "quick click" on a mouse button. By a "quick click" is understood a click on a mouse button executed within a certain time interval, for example with 0.5 seconds. I.e. the mouse button is activated in a time period less than the specified time interval. If the click execution is slower (i.e. the mouse button is activated in a time period longer than the specified time interval) nothing will happen. The time interval may be predefined and/or may be specified by a user. This "quick click" feature greatly enhances the dental restoration modeling experience for the user. Within seconds the dental restoration model can be dragged, widened, tilted and/or rotated by just few clicks on the mouse.

However, not all possible functionalities of a control point are always relevant. For example when the dental model and the dental restoration model are seen from the side. In this case a rotation of the dental restoration around the long axis is irrelevant to the user. And when a dental restoration model is seen from the top a variation of the height of the dental restoration is also irrelevant for the user. Thus, in a preferred embodiment of the invention the functionality of at least one control point is depending on the orientation of the dental restoration model. I.e., orientation in the meaning of the view angle of the dental restoration model seen by the user.

The orientation of the dental model and the dental restoration model is also relevant in other circumstances. The user will typically shape the dental restoration model when viewed along with the dental model. However, because the dental restoration is typically located between adjacent teeth the dental model can block the view of the dental restoration model for the user for certain view angles. Thus, the display of at least a part of the dental model is preferably depending of the orientation of the dental model, i.e. the view angle for the user. This dental restoration view blocking can preferably be solved by letting at least part of the dental model be invisible for certain orientations, preferably the invisible part of the dental model is the part that is between the user and the dental restoration model. Thereby the dental restoration model can be seen by the user for any orientation of the dental model.

In one embodiment of the invention the control points of the dental restoration model are a central part of the system. However, the appearance of all the control points can disturb the image of the dental restoration model when trying to create the perfect fit into the dental model. In a preferred embodiment of the invention the control points are only visible when the mouse marker (cursor) is within a specific distance from the dental restoration model. This specific distance can be a specific number of pixels on the screen or a specific distance related to the dental model and the dental restoration model. The dental model is a replica of a patient's teeth, thus the specific dimensions of the dental model are known exactly and at least one coordinate system is embedded in the system according to the disclosure. Thus, it can be specified in the system that the control points are only visible when the mouse marker is within a distance of a specific number of millimeters.

In specific embodiments of the invention the control points are only visible when the mouse cursor is within a distance of preferably 10 pixels from the dental restoration model, such as within a distance of 500 pixels, such as within a distance of 300 pixels, such as within a distance of 200 pixels, such as within a distance of 100 pixels, such as within a distance of 80 pixels, such as within a distance of 60 pixels, such as within a distance of 40 pixels, such as within a distance of 30 pixels, such as within a distance of 20 pixels, such as within a distance of 15 pixels, such as within a distance of 12 pixels, such as within a distance of 8 pixels, such as within a distance of 6 pixels, such as within a distance of 5 pixels, such as within a distance of 4 pixels, such as within a distance of 3 pixels, such as within a distance of 2 pixels, such as within a distance of 1 pixel from the dental restoration model.

A situation where the user is working on at least two dental restoration models in the same dental model can occur. This can for example be the case when two adjacent abutments are being designed. In this case the appearance of control points in both dental restoration models can confuse the image for the user. This can preferably be overcome by only showing the control points on the dental restoration model closest to the mouse marker.

A significant part of a dental restoration may be located below the gingival, especially when the dental restoration mode is an abutment model. Thus, when customizing a dental restoration model in a dental model, a part of the dental restoration model is hidden by the gingival of the dental model. It was previously indicated that if the dental model is blocking the view of the dental restoration model the blocking part of the dental model would advantageously become invisible to the user. However this is not a good solution in all cases, because if the dental model was invisible when trying to shape the dental restoration model to fit into the gingival of dental model, a perfect fit would be almost impossible. This can be solved by changing the transparency of the dental model. Thus, in a preferred embodiment of the invention the transparency of the dental model is variable. The transparency of the dental model is preferably automatically adjusted when needed, for example when the mouse cursor is close to a control point below the surface of the dental model. This is very helpful to the user, because the entire dental restoration model and the control points are thereby visible and the dental restoration model can be shaped to fit a dental model that is still visible but transparent. The transparency can for example be adjusted to 50%, where 0% transparency is the normal image, i.e. see through is impossible, and 100% transparency is totally invisible.

The systems and methods according to the disclosure furthermore regard the embodiments wherein the dental restoration is an implant abutment, a coping, a crown and/or any combination of these. Correspondingly, the disclosure regards the embodiments wherein a dental restoration model is an abutment model, a coping model, a crown model or any combination of these.

The disclosure furthermore includes a computer program product having a computer readable medium, said computer program product comprising means for carrying out any of the listed methods.

DESCRIPTION OF DRAWINGS

The disclosure will now be explained in greater details with reference to the figures showing embodiments of the invention where the dental restoration is one or more abutments.

DETAILED DESCRIPTION OF THE PREFERRED EMBODIMENTS

Figure 1:
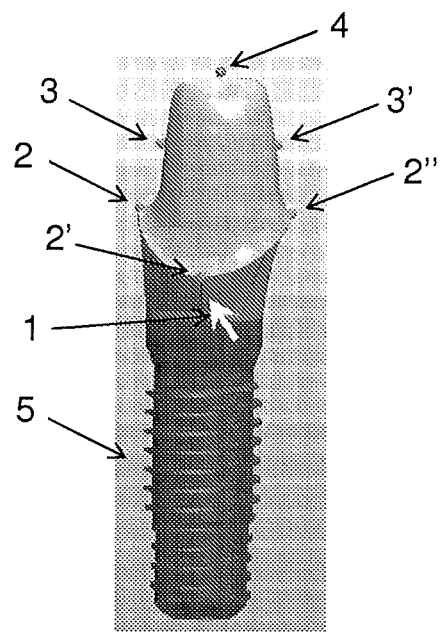
FIG. 1 shows a 3D model of a dental restoration model, in this case an implant abutment with 6 control points, the mouse marker is close to the abutment.
Figure 2:
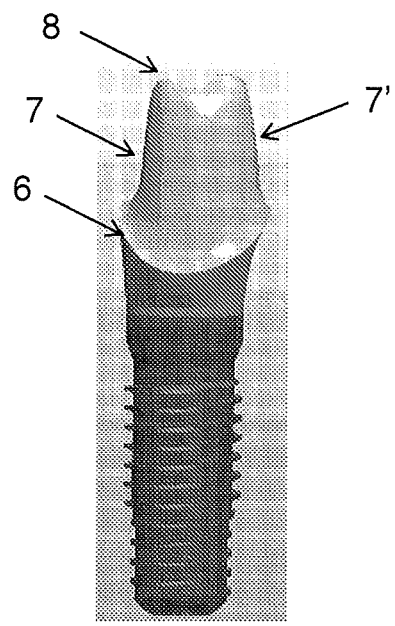
FIG. 2 shows a 3D model of the abutment in FIG. 1, but the control points are hidden because the mouse marker is not near the abutment.

A 3D model of an implant abutment is shown in FIGS. 1 and 2. When the finished abutment is inserted into the mouth of the patient, the threaded part 5 of the abutment goes into the jaw of the patient with the collar 6 just below the gingival. A crown is glued onto the abutment. In FIG. 2 the sides 7, 7' and the top part 8 of the abutment is indicated. In FIG. 1 an abutment model corresponding to the abutment model in FIG. 2 is shown along with a plurality of control points, 2, 2', 2", 3, 3', 4. The control points are located along the edges of the abutment model, i.e. round the collar 2, 2', 2", at the sides 3, 3' and at the top 4 of the abutment model. The control points are visible because the mouse cursor 1 is near the abutment model. In most of the figures the mouse cursor 1 is represented by a white arrow pointing up and left.

Figure 3:
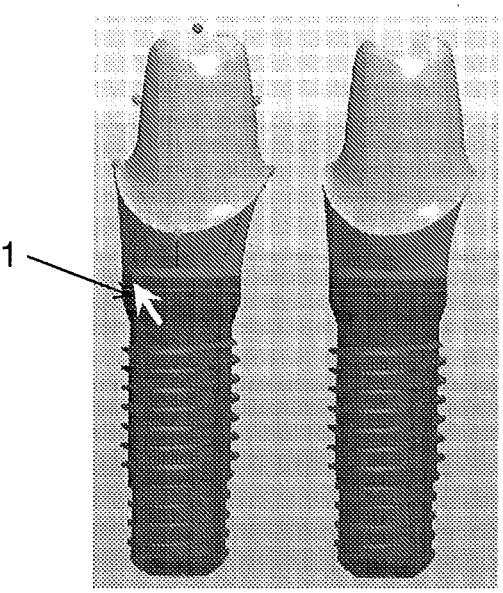
FIG. 3 shows two abutments with control points on only the left abutment where the mouse marker is located.

FIG. 3 shows two adjacent abutment models, however control points are only visible at the left abutment model because the mouse cursor 1 is located at said left abutment model.

Figure 4:
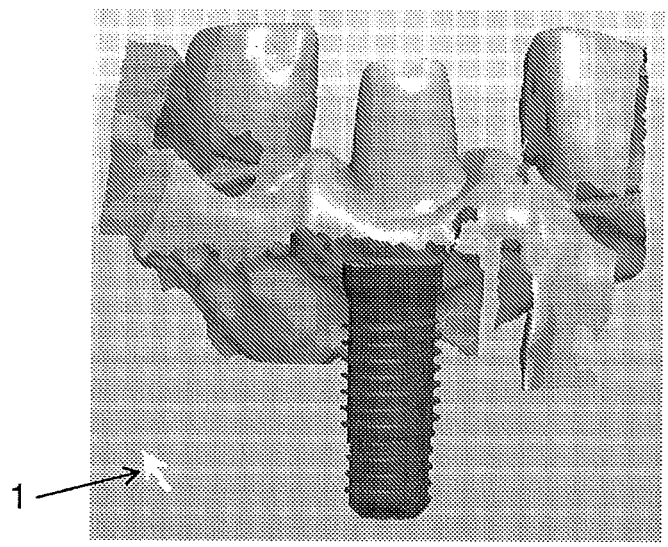
FIG. 4 shows an abutment surrounded and partly hidden by a dental model.
Figure 5:
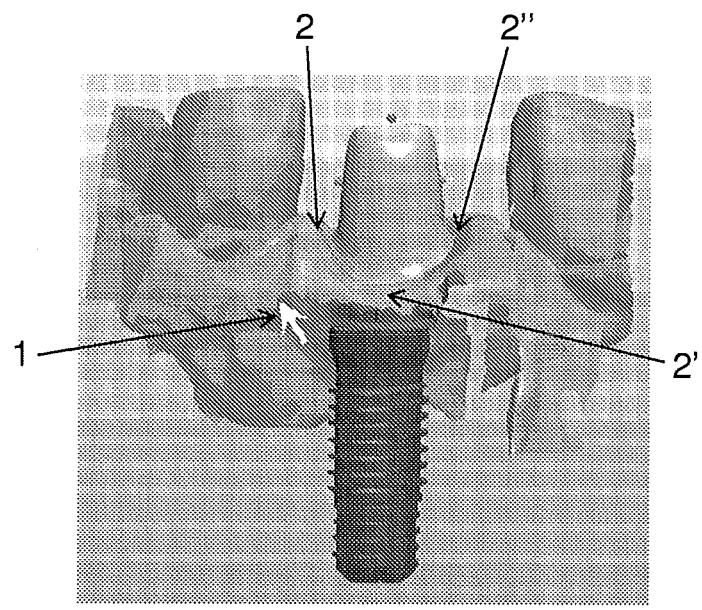
FIG. 5 shows the abutment in FIG. 4; when the mouse marker is close to the abutment the dental model becomes transparent whereby control points beneath the surface of the dental model become visible.

FIG. 4 shows an abutment model surrounded by a dental model wherein the abutment model must be fitted. The mouse cursor 1 is in the bottom left corner of FIG. 4. Part of the abutment model is hidden below the dental model, e.g. the collar of the abutment model is invisible. FIG. 5 shows the abutment and dental model of FIG. 4 when the mouse cursor 1 is near the abutment model. The control points are now visible, also the three control points 2, 2', 2" round the collar of the abutment model, and the transparency of the dental model has changed whereby the previously hidden parts of the abutment model is now visible through the dental model.

Figure 6:
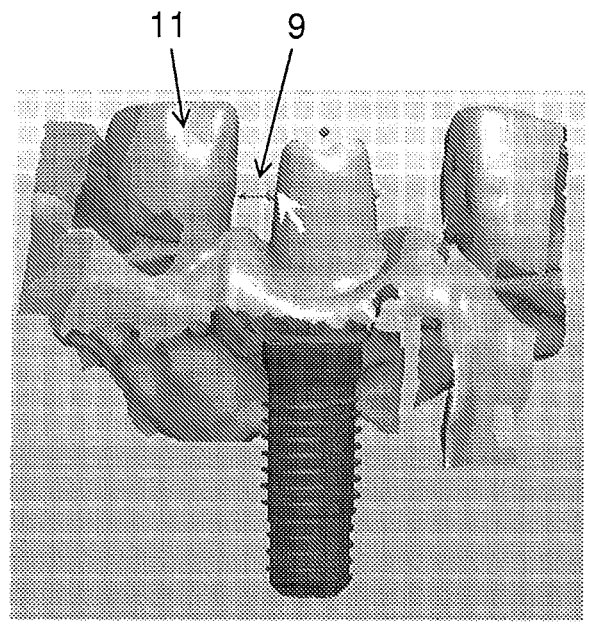
FIG. 6 shows an arrow in one of the control points, the arrow having a user defined length indicating the distance between an implant abutment and the adjacent tooth in the surrounding dental model.

FIG. 6 shows an abutment model surrounded by a dental model with visible control points. The mouse cursor is very close to one of the control points along the left side of the abutment, whereby an arrow 9 is visible. The length of the arrow 9 can be defined by the user, the length defined as the length from the origin to the tip of the arrow, the origin being the edge of the abutment model at the control point. The arrow 9 can thereby indicate a distance from the abutment to an object. In FIG. 6 the arrow 9 is indicating the distance from the abutment to the adjacent tooth 11. Thus when customizing the abutment model, e.g. widening the abutment model by dragging the model in a control point, the arrow 9 can in real-time (i.e. concurrently with dragging the model) indicate the distance to the neighboring tooth.

Figure 7:
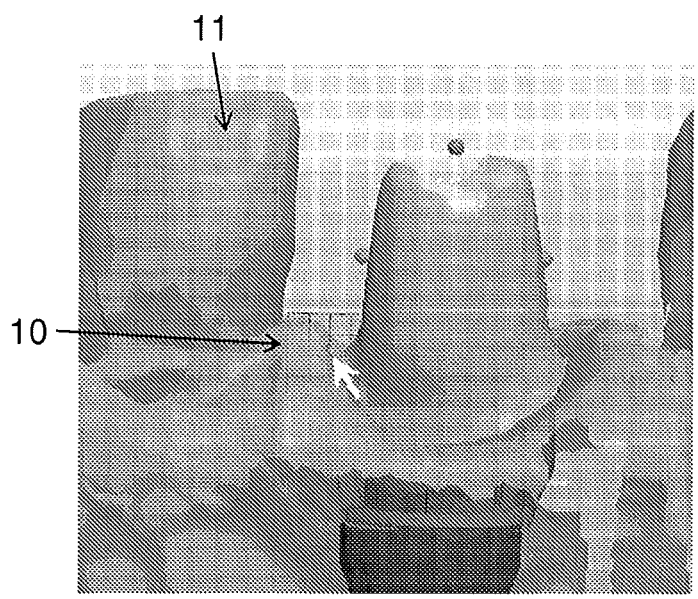
FIGS. 7 & 8 show a grid in a control point, the grid having user defined partitions into squares indicating the distance between an implant abutment and the adjacent tooth (FIG. 7) and the gingival ridge (FIG. 8) respectively.
Figure 8:
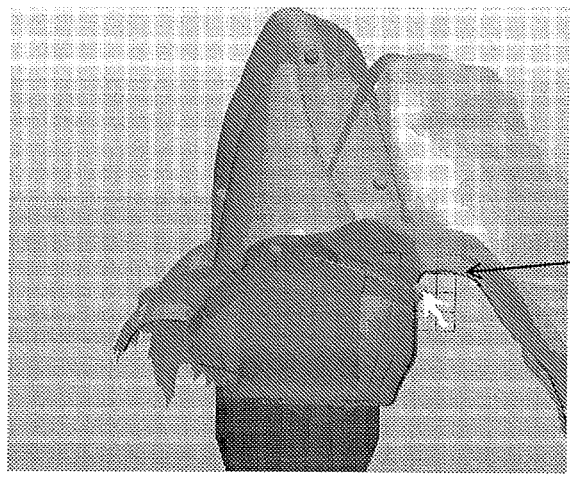

FIG. 7 shows a close up of an abutment model in a partly transparent dental model. The mouse cursor is close to a control point at the collar of the abutment model thereby initiating the display of the grid 10. The size of the grid 10 is preferably defined by the user, the size being the length of the sides of the grid. The arrow 9 shown in FIG. 6 can indicate direct distances, whereas the grid 10 can indicate projected distances. For example the collar of an abutment must be a certain distance below the gingival. However the gingival might not be directly above the collar of the abutment. By the grid 10 shown in FIG. 7 the orthographic projection from the top of the gingival between teeth to the abutment collar represented by a control point is indicated. Another example is shown in FIG. 8 where a grid is shown to indicate the orthographically projected distance between the abutment collar represented by a control point and the gingival ridge 12.

Figure 9:
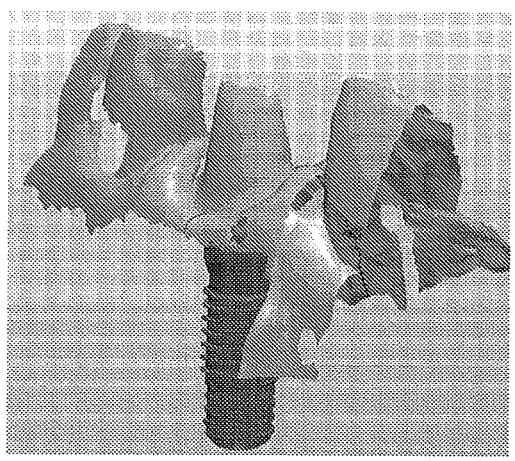
FIG. 9 shows an abutment and the surrounding dental model.
Figure 10:
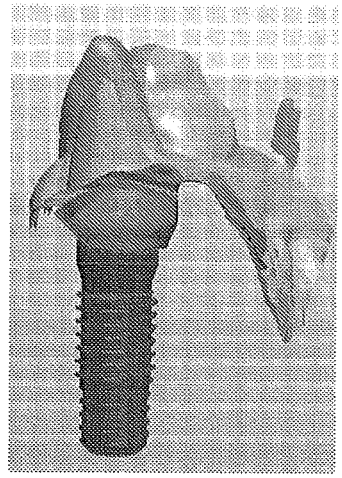
FIG. 10 is a rotated view of FIG. 9 where the part of the dental model obstructing a user the view of the abutment is invisible.

FIG. 9 shows an abutment model surrounded by a dental model. If the view angle of these models was changed, e.g. by the user, the dental model would hide the abutment model when seen from the side. However, as shown in FIG. 10, the system and method according to the disclosure can provide for that part of the dental model becomes invisible when blocking the view to the abutment model.

Figure 11:
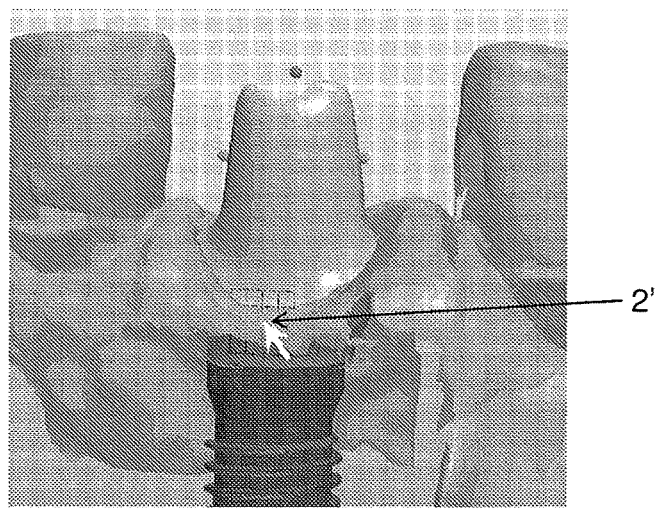
FIG. 11 shows an abutment surrounded by a dental model and a grid at one of the lower control points with a translational functionality.
Figure 12:
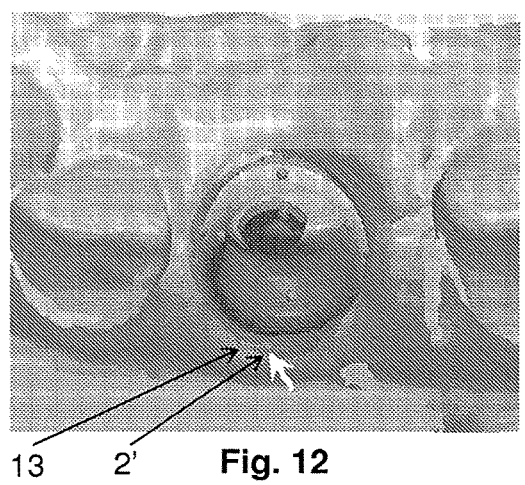
FIG. 12 shows the abutment in FIG. 13 rotated to a top view where the control point, that in FIG. 13 was a translational control point and displaying a grid when activated, has now changed functionality to become a rotational control point because of the changed point of view.
Figure 13:
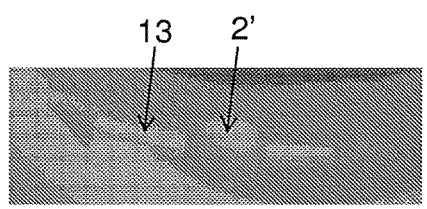
FIG. 13 shows a close up of a control point in FIG. 12.

FIG. 11 shows an abutment model displaying a grid at a control point 2' at the abutment collar and near the mouse cursor. FIG. 12 shows the corresponding abutment model seen from above with the identical control point 2'. Near said control point 2' is no longer a grid because a grid would be irrelevant to the customization of the abutment model when the abutment model is seen from above. Instead a curved double-arrow 13 is shown near the control point 2'. This can be seen more clearly in FIG. 13, which is a close up of the control point 2' and the arrow 13 in FIG. 12. By dragging the control point 2' the abutment model can be rotated. This rotation can be necessary to align the top ridge of the abutment model with top ridges of adjacent teeth. Thus, the control point 2' has different functionalities depending on the orientation, i.e. the view angle for the user, of the abutment and dental models. Thereby the necessary number of displayed control points can be reduced, i.e. simplifying the view for the user and increasing the user-friendliness.

Figure 14:
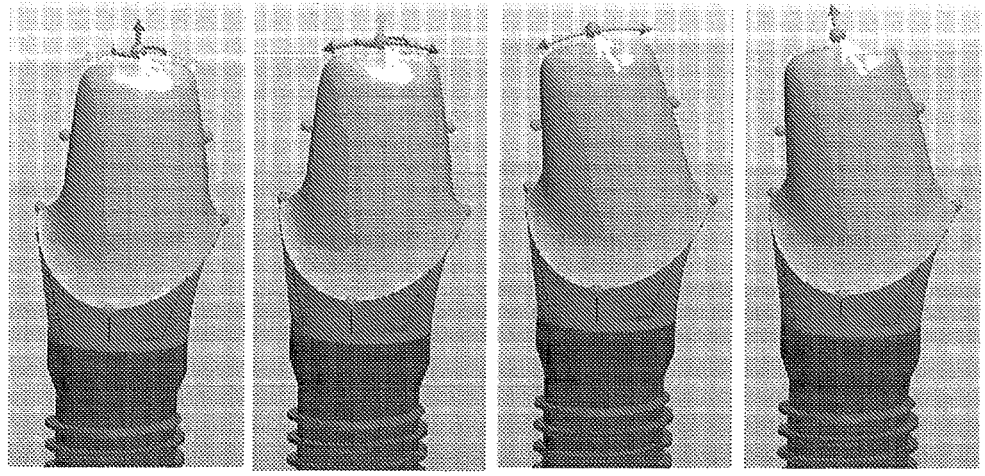
FIG. 14 shows four views of the same abutment being customized, the control points in the top part shift functionality.

FIG. 14 shows the same abutment model four times illustrating that a control point can have different functionalities independent of the orientation of the abutment model. To the left the control point at the top of the abutment model has the functionality of increasing the height of the abutment model. The functionality is illustrated by a symbol with an arrow pointing up. However by just a single click on the mouse the functionality of the top control point in the second picture from the left has changed functionality to "tilt", i.e. the abutment model can be tilted from side to side by dragging the control point. The tilt functionality is illustrated by arrows pointing to each side along the top edge of the abutment model. In the third picture from the left the abutment model has been tilted to the left and in the rightmost picture the functionality of the control point is changed back into variation of the height. This shift of functionality of a control point could very well be provided by other means, i.e. a drop down menu in the GUI or the like. However, by the preferred method of changing the functionality by a single click with the mouse, the design process is kept quick and simple, because the user does not have to move the mouse cursor on the screen, but can just keep the mouse cursor on one control point.

Figure 15:
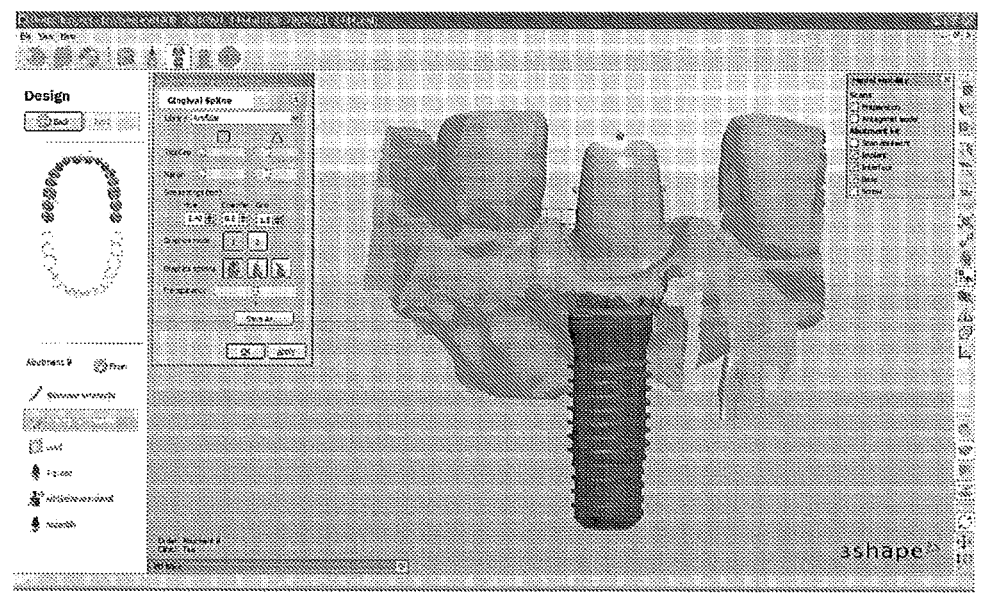
FIG. 15 is a screen shot of the system according to one embodiment of the invention.

FIG. 15 is a screenshot example from one embodiment of the invention showing an abutment model surrounded by a dental model and a plurality of the menus, buttons and the like, all part of the GUI of the system. This is normal for any graphics design system. However, by the system and methods according to the disclosure the user-friendliness has been improved, because a plurality of features/tools that would normally be provided or changed by means of buttons and pull-down menus, in this case is automatically provided or provided by a few clicks on a mouse button.

The invention claimed is:

1. A non-transitory computer readable medium embedded with a computer program providing a graphical user interface for a computer system for designing at least one dental restoration by a method comprising:

displaying on a display of the computer system a three dimensional dental restoration model of the dental restoration, and providing a plurality of control points at the dental restoration model, each of the control points corresponding to a respective location on the dental restoration model and each of said control points being user-adjustable to manually customize the dental restoration model, wherein at least one of the control points is activated by moving a mouse cursor within a predetermined distance of the at least one control point, wherein the control point is activated by moving the mouse cursor within a distance of 10 pixels from the control point.

2. A non-transitory computer readable medium embedded with a computer program providing a graphical user interface for a computer system for designing at least one dental restoration by a method comprising:

displaying on a display of the computer system a three dimensional dental restoration model of the dental restoration, and providing a plurality of control points at the dental restoration model, each of the control points corresponding to a respective location on the dental restoration model and each of said control points being user-adjustable to manually customize the dental restoration model, wherein at least one of the control points is activated by moving a mouse cursor within a predetermined distance of the at least one control point, wherein the control points only are visible when a mouse cursor is within a distance of 10 pixels from the dental restoration model.

3. A non-transitory computer readable medium embedded with a computer program providing a graphical user interface for a computer system for designing at least one dental restoration by a method comprising:

displaying on a display of the computer system a three dimensional dental restoration model of the dental restoration, and providing a plurality of control points at the dental restoration model, each of the control points corresponding to a respective location on the dental restoration model and each of said control points being user-adjustable to manually customize the dental restoration model, wherein at least one of the control points is activated by moving a mouse cursor within a predetermined distance of the at least one control point, wherein only the control points of the dental restoration model closest to a mouse cursor are visible when two or more dental restoration models are shown simultaneously.

4. A non-transitory computer readable medium embedded with a computer program providing a graphical user interface for a computer system for designing at least one dental restoration by a method comprising:

displaying on a display of the computer system a three dimensional dental restoration model of the dental restoration, and providing a plurality of control points at the dental restoration model, each of the control points corresponding to a respective location on the dental restoration model and each of said control points being user-adjustable to manually customize the dental restoration model, wherein at least one of the control points is activated by moving a mouse cursor within a predetermined distance of the at least one control point, wherein the method further comprises displaying on the display an arrow or a grid at at least one of the control points, if an arrow, then a length of said arrow is determined by a user defined value, whereby a distance between the dental restoration model and neighboring objects is indicated; and, if a grid, then a size of said grid is determined by a user defined value, whereby the distance between the dental restoration model and neighboring objects is indicated.

5. The computer readable medium according to claim 4, wherein the arrow or the grid of a control point is only displayed when said control point is activated.

6. The computer readable medium according to claim 4, wherein the length of the arrow or the size of the grid of a control point is adjustable when the control point is activated.

7. A non-transitory computer readable medium embedded with a computer program providing a graphical user interface for a computer system for designing at least one dental restoration by a method comprising:

displaying on a display of the computer system a three dimensional dental restoration model of the dental restoration, and providing a plurality of control points at the dental restoration model, each of the control points corresponding to a respective location on the dental restoration model and each of said control points being user-adjustable to manually customize the dental restoration model, wherein at least one of the control points is activated by moving a mouse cursor within a predetermined distance of the at least one control point, wherein the at least one of the control points is only displayed when the mouse cursor is within the predetermined distance of the at least one of the control points.

8. The computer readable medium according to claim 7, wherein a functionality of at least one control point can be changed by a user when said control point is activated.

9. The computer readable medium according to claim 7, wherein a functionality of at least one control point depends on the orientation of the dental restoration model.

10. The computer readable medium according to claim 7, wherein the method comprises displaying on the display a three dimensional dental model of the patient's teeth in which three dimensional dental model the dental restoration must be fitted.

11. The computer readable medium according to claim 10, wherein the graphical user interface is configured to provide that the dental restoration model is viewable through the dental model.

12. The computer readable medium according to claim 10, wherein at least a part of the dental model is invisible when said part of the dental model is in front of the dental restoration model such that the dental restoration model is viewable and accessible for the user.

13. The computer readable medium according to claim 10, wherein transparency of the dental model is increased when a mouse cursor is close to a control point beneath an occluding surface of the dental model, whereby the control point and the dental restoration model can be seen through the dental model.

14. The computer readable medium according to claim 7, wherein the control points are located at the edges of the dental restoration model.

15. The computer readable medium according to claim 7, wherein the dental restoration is selected from the group consisting of an implant abutment, a coping and a tooth crown.

16. A non-transitory computer-readable medium encoded with a computer program that causes a computer system to perform the following operations:

display on a display device of the computer system a three-dimensional dental restoration model of a dental restoration;

providing a plurality of control points at the dental restoration model, each of the control points corresponding to a respective location on the dental restoration model; and in response to user movement of a control point displayed on the display device, changing an attribute of the dental restoration model at the location corresponding to the control point, to provide a dental restoration model for manufacturing a customized dental restoration, wherein at least one of the control points is displayed by activating by moving a mouse cursor within a predetermined distance of the at least one control point.

17. The computer-readable medium of claim 16, wherein the attribute is a dimension of the dental restoration model.

18. The computer-readable medium of claim 16, wherein the attribute is a shape of the dental restoration model.

19. The computer-readable medium of claim 16, wherein the attribute is an orientation of the dental restoration model.

20. A non-transitory computer-readable medium encoded with a computer program that causes a computer system to perform the following operations:

display on a display device of the computer system a three-dimensional dental restoration model of a dental restoration;

display on the display device a plurality of control points at the dental restoration model, each of the control points corresponding to a respective location on the dental restoration model; and in response to user movement within a predetermined distance from a control point displayed on the display device:

displaying an arrow adjacent to the dental restoration model, the length of said arrow determined by a user defined value, whereby the distance between the dental restoration model and neighboring objects can be measured or indicated; or displaying a grid adjacent to the dental restoration model, the size of said grid determined by a user defined value, whereby the distance to neighboring objects can be indicated, to provide a dental restoration model for manufacturing a customized dental restoration.

21. The computer readable medium of claim 20, wherein the control point is activated by moving a mouse cursor within a distance of 10 pixels from the control point.

22. The computer readable medium of claim 20, wherein the control points only are visible when a mouse cursor is within a distance of 10 pixels from the dental restoration model.

23. The computer readable medium of claim 20, wherein only the control points of the dental restoration model closest to a mouse cursor are visible when two or more dental restoration models are shown simultaneously.

24. A non-transitory computer readable medium embedded with a computer program providing a graphical user interface for a computer system for designing at least one dental restoration by a method comprising:
- displaying on a display of the computer system a three dimensional dental restoration model of the dental restoration, and
- providing a plurality of control points at the dental restoration model, each of the control points corresponding to a respective location on the dental restoration model and each of said control points being user-adjustable to manually customize the dental restoration model,
- wherein at least one of the control points is activated by moving a mouse cursor within a predetermined distance of the at least one control point,
- wherein the method further comprises displaying on the display an arrow or a grid at the at least one of the control points only when the at least one of the control points is activated.

25. The computer readable medium according to claim 7, wherein a functionality of at least one control point is variable.

26. The computer readable medium according to claim 7, wherein a functionality of the at least one control point is variable.

27. The computer readable medium according to claim 26, wherein the functionality of the at least one control point can be changed by a user when said control point is activated.

28. The computer readable medium according to claim 26, wherein providing the control points includes displaying the control points at the dental restoration model.

29. A method of providing a graphical user interface for a computer system for designing at least one dental restoration by a method comprising:
- displaying on a display of the computer system a three dimensional dental restoration model of the dental restoration, and
- providing a plurality of control points at the dental restoration model, each of the control points corresponding to a respective location on the dental restoration model and each of said control points being user-adjustable to manually customize the dental restoration model,
- wherein at least one of the control points is only visible on the display when the mouse cursor is within a predetermined distance of the at least one of the control point.

* * * * *